(12) United States Patent
George et al.

(10) Patent No.: US 7,963,909 B2
(45) Date of Patent: Jun. 21, 2011

(54) METHODS OF MANUFACTURING FLUID RESERVOIRS FOR PENILE IMPLANT DEVICES

(75) Inventors: Stephanie A. George, St. Louis Park, MN (US); Jon D. Albrecht, Hutchinson, MN (US); Robert L. Rykhus, Edina, MN (US); Randy L. Morningstar, Brooklyn Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 12/727,301

(22) Filed: Mar. 19, 2010

(65) Prior Publication Data

US 2010/0171236 A1 Jul. 8, 2010

Related U.S. Application Data

(62) Division of application No. 10/957,190, filed on Oct. 1, 2004, now Pat. No. 7,717,845.

(60) Provisional application No. 60/507,972, filed on Oct. 2, 2003, provisional application No. 60/507,974, filed on Oct. 2, 2003.

(51) Int. Cl.
*A61F 5/00* (2006.01)

(52) U.S. Cl. ....................................................... 600/40

(58) Field of Classification Search ............... 600/38–41; 425/6; 264/4, 5, 239–241, 328.1–328.2
See application file for complete search history.

(56) References Cited

U.S. PATENT DOCUMENTS

| 4,566,446 | A | 1/1986 | Fogarty |
| 4,602,625 | A | 7/1986 | Yachia et al. |
| 5,048,511 | A | 9/1991 | Rosenbluth et al. |
| 5,704,895 | A | 1/1998 | Scott et al. |
| 6,534,112 | B1 | 3/2003 | Bouchier et al. |
| 6,558,315 | B1 | 5/2003 | Kuyava |
| 2003/0028076 | A1 | 2/2003 | Kuyava et al. |
| 2003/0220540 | A1 | 11/2003 | Kuyava |
| 2004/0040500 | A1 | 3/2004 | Bouchier et al. |

*Primary Examiner* — John P Lacyk
(74) *Attorney, Agent, or Firm* — Kimberly K. Baxter; Gregory L. Koeller (57) ABSTRACT

A fluid reservoir for a penile implant device that includes a body portion having a sleeve from which a tube may extend. The body portion includes support structure positioned at an interior surface of the body portion near an orifice of the reservoir, which orifice leads to a fluid passage of the tube. The support structure may comprise a plurality of protrusions that are arranged around the orifice and that extend from a base portion of the body portion. The invention also relates to a method of manufacturing a fluid reservoir for a penile implant device, which includes positioning a tube in a mold and injection molding a reservoir body onto the tube. More particularly, the method may include providing a mold, positioning a tube in the mold, injecting material into the mold, curing the material, and opening the mold to remove the reservoir body and tube assembly.

6 Claims, 11 Drawing Sheets

METHODS OF MANUFACTURING FLUID RESERVOIRS FOR PENILE IMPLANT DEVICES

CROSS REFERENCE TO RELATED APPLICATIONS

This application is a divisional application of U.S. patent application Ser. No. 10/957,190, filed Oct. 1, 2004 now U.S. Pat. No. 7,717,845, now allowed, which claims the benefit of U.S. Provisional applications having Ser. No. 60/507,972, filed Oct. 2, 2003, entitled "FLUID RESERVOIRS FOR PENILE IMPLANT DEVICES AND METHODS OF MANUFACTURING", and Ser. No. 60/507,974, filed Oct. 2, 2003, entitled "PENILE IMPLANT RESERVOIRS AND METHODS OF MANUFACTURING", which applications are incorporated herein by reference in their entireties.

TECHNICAL FIELD

The present invention relates generally to surgical implant devices and methods of making such devices. More particularly, the present invention relates to fluid reservoirs for use with penile implant devices and methods of making such reservoirs.

BACKGROUND OF THE INVENTION

One common treatment for erectile dysfunction includes the use of a penile implant device. One type of penile implant device, commonly known as a three-piece device, includes a pair of inflatable cylindrical prostheses that are implanted into the corpus cavernosae of the penis, which are connected to a fluid-filled reservoir through a pump and valve assembly. Such a pump and valve assembly is typically implanted into the scrotum of the patient, and the reservoir is implanted in the abdomen. Tubing is used to connect each penile prosthesis to the pump, and additional tubing is used to connect the pump to the reservoir. To activate the penile implant device, the patient would typically actuate the pump using one of a variety of methods that cause fluid to be transferred from the reservoir through the pump and into the prostheses. This results in the inflation of the prostheses and produces rigidity for a normal erection. Then, when the patient desires to deflate the prostheses, a valve assembly within the pump is actuated in a manner such that the fluid in the prostheses is released back into the reservoir. This deflation returns the penis to a flaccid state.

The reservoir used in these three-piece systems is usually in the form of a flexible bag or bladder that can expand and contract in volume with movement of fluid to and from the reservoir. One commonly used method for manufacturing these reservoirs is by a dip coating process. Dip coating consists of introducing a mandrel of a desired geometry into a self-leveling thermoplastic or thermosetting material (e.g., a silicone dispersion of a specific solids content and viscosity). Much like old-fashioned candle making, the mandrel is repeatedly dipped into the dispersion until a desired wall thickness is obtained for the part. A period of time (e.g., 15 to 20 minutes) can be required between successive dipping processes to allow the previous coat of material to set sufficiently before initiating the next successive dip cycle. In the case of a spherical reservoir, for example, 24 to 28 dip cycles may be required to obtain a suitable wall thickness.

After a desired wall thickness is achieved, the reservoir produced by the mandrel coating process may be subjected to additional processing steps, such as placement in an oven for a curing process, for example. Curing is a step that is typically used in a process of preparing a thermosetting (e.g., silicone) reservoir body of a penile implant device. In some cases, an oven curing process can take a significant amount of time, such as 6 to 8 hours. After the curing process is complete, the coated mandrel is removed from the oven and allowed to cool to room temperature. The cured reservoir is then manually removed from the mandrel to complete the process. The total time from start to finish for a dip coating process can be 24 hours or more, and can be very costly and labor intensive. In addition, the dip coating process can require a relatively large manufacturing area, particularly when many reservoirs are being manufactured simultaneously.

The materials used for making reservoirs by dip-coating processes can also be expensive and time consuming to prepare, which further increases the cost and timing of producing a dip-coated implantable reservoir. One example of a material that is sometimes used in these dip-coating processes is a silicone dispersion that is a two-part platinum cure dispersion dispersed in xylene to convert from a semi-solid to a self-leveling liquid state. Preparation of the dispersion before it can be used for a dip-coating process can take 24 hours or longer, including the time required for mixing and de-airing. For manufacturing efficiency, the batches of material are generally made in relatively large quantities, which are usually very expensive. The effective cost of the dispersion further increases in cases where a portion of the dispersion is unused and must be discarded after its predetermined usable life.

The production of dip-coated implantable reservoirs also can be relatively complicated due to the number of parts and bonds required to incorporate the reservoir into a device that can be used in a prosthesis device. As an example, four components are often used to produce a typical dip coated reservoir assembly. These components include a molded silicone shell adapter, a silicone stand pipe, a dip coated reservoir shell, and section of kink resistant tubing. In this reservoir assembly, each of the individual components is bonded to an adjacent component using a suitable adhesive, such as a medical grade silicone adhesive. Each time a bond is made, an air (ambient) cure is performed, which generally take at least thirty minutes or longer, and which is followed by an oven cure generally for sixty minutes or longer before proceeding to the next bonding operation, thereby resulting in a process that is relatively slow, and time consuming. Thus, it is desirable to produce reservoir assemblies by methods and materials that are less costly than the production of reservoir assemblies using the dip coating and bonding methods described above.

SUMMARY OF THE INVENTION

The invention relates to methods and devices that overcome certain shortcoming of prior fluid reservoirs for penile implant devices, and to methods of manufacturing reservoir components (e.g., reservoir shells) and methods of incorporating the components (e.g., support structures) into an implantable prosthesis device. The invention provides fluid reservoirs for such devices that have improved manufacturability, improved fluid flow properties, or preferably both.

The invention can include the use of injection molding processes to produce a fluid reservoir body for a penile implant device. Injection molding can eliminate multiple steps and the substantial time that can be required to produce a reservoir by dip coating methods. In particular, injection molding methods can reduce the timing required to apply multiple coats of material during a dip coating method, and additionally can be used to produce a reservoir assembly that include fewer pieces, thus requiring fewer bonding steps.

Another aspect of the invention can include a structure for an implantable reservoir that includes a support structure (e.g., in the form of multiple protrusions) at the base of the inside of the reservoir near an exit orifice. The support structure can prevent the reservoir from collapsing during use such that a surface of the reservoir would cover the exit orifice. The support structure can preferably be included in a reservoir body that is prepared by an injection molding method.

In one aspect, the invention relates to a fluid reservoir for a penile implant device that includes a body portion having a sleeve from which a tube may extend. The body portion includes support structure positioned at an interior surface of the body portion near an orifice of the reservoir, which orifice leads to a fluid passage of the tube. In preferred embodiments, the support structure may comprise a plurality of protrusions that are arranged around the orifice and that extend from a base portion of the body portion.

In another aspect, the invention relates to a method of manufacturing a fluid reservoir for a penile implant device, including a step of injection molding a reservoir body. A preferred method can include positioning a tube in a mold and injection molding a reservoir body onto the tube. More particularly, the method may include providing a mold, positioning a tube in the mold, injecting material into the mold, curing the material, and opening the mold to remove the reservoir body and tube assembly.

The present invention also relates to methods and devices that overcome certain shortcoming of prior fluid reservoirs for penile implant devices by providing fluid reservoir structures for such devices that have improved fatigue resistance. The present invention also relates to methods and devices that provide fluid reservoir structures that include flow control structures.

In another aspect of the invention, a fluid reservoir for a penile implant device includes a shell, an adapter, and preferably a tube. The shell has an annular neck portion that defines an opening. The annular neck portion mates with an annular groove and a flange of the adapter to form a gradual transition from the adapter to the wall of the shell. Such a transition can help to control compliance mismatch between the adapter and shell and thereby provide improved reliability such as by providing a more gradual change in wall thickness for improved fatigue resistance. The tube is preferably attached to the adapter to provide a fluid passage that can be connected to another component of a penile implant device.

In another aspect, the invention relates to a fluid reservoir for a penile implant device that includes a shell portion, an adapter portion, and preferably a tube. The shell includes a plurality of elements such as ridges formed on an inside surface of the shell. The ridges are positioned near a transition between the adapter and the shell. Such ridges can provide improved fatigue resistance by providing a smooth transition between the adapter and the shell.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE PREFERRED EMBODIMENTS

Figure 1:
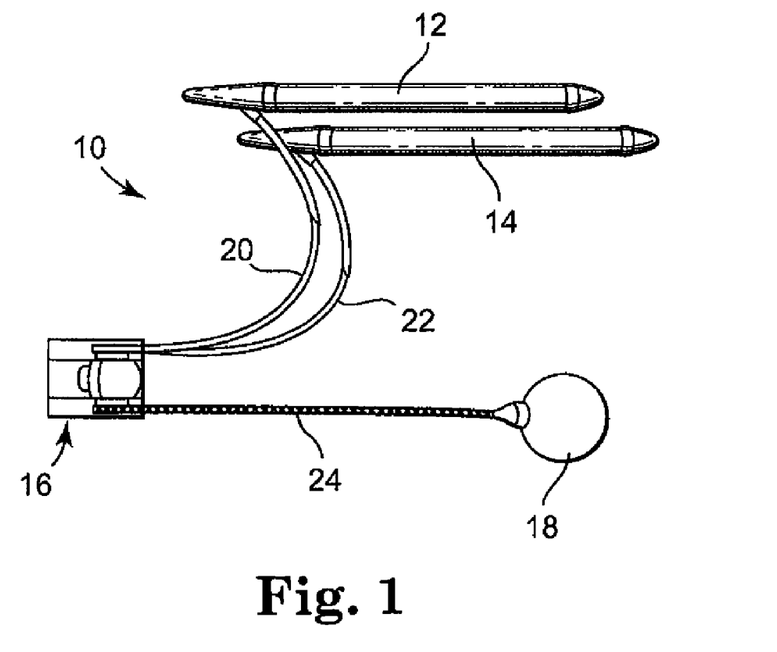
FIG. 1 is a top view of a three-piece implantable penile prosthesis device having a pair of penile prostheses, a pump, and a reservoir of the present invention.

Referring now to the Figures, wherein the components are labeled with like numerals throughout the several Figures, and initially to FIG. 1, one preferred configuration of a surgically implantable penile prosthesis device 10 having a three-piece design is illustrated. As shown, the device 10 generally includes first and second inflatable penile cylinders 12 and 14, respectively, a pump 16, and a reservoir 18 in accordance with the present invention. The first penile cylinder 12 is fluidly coupled to the pump 16 by a tube 20 and the second penile cylinder 14 is fluidly coupled to the pump 16 by a tube 22. The pump 16 is fluidly coupled to the reservoir 18 by a tube 24. Typically, the cylinders 12 and 14 are surgically implanted into the corpus cavernosa regions of a penis and the pump 16 is implanted within the scrotum of a patient, while the reservoir 18 is usually implanted within the abdomen of the patient. In use, the patient can activate the pump 16 in some manner (e.g., squeezing the pump 16 in a particular way to open a valve) to move fluid from the reservoir 18 to inflate the penile cylinders 12 and 14 and provide an erection. Similarly, the patient can activate the pump 16 to return fluid to the reservoir 18 and thereby deflate the penile cylinders 12 and 14 and return the cylinders to a flaccid condition. A wide variety of configurations of penile prosthesis devices may utilize a reservoir 18 of the type described herein, however, where the device 10 of FIG. 1 is intended to illustrate one representative system in which a reservoir 18 may be used. For example, a number of different types of pump configurations may be used, such as those that require very little manipulation to move fluid between the reservoir and cylinders, or those that instead require the user to repeatedly squeeze the pump body for fluid transfer within the penile prosthesis device or system. In addition, devices having greater or fewer components than are used in a three-piece design can utilize the advantages of the reservoirs of the present invention.

Figure 2:
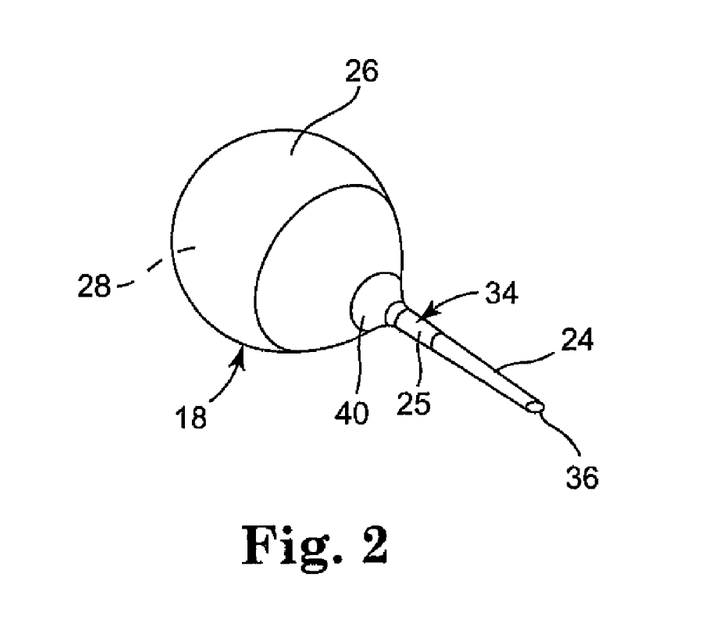
FIG. 2 is a perspective view of one embodiment of a reservoir of the present invention.
Figure 3:
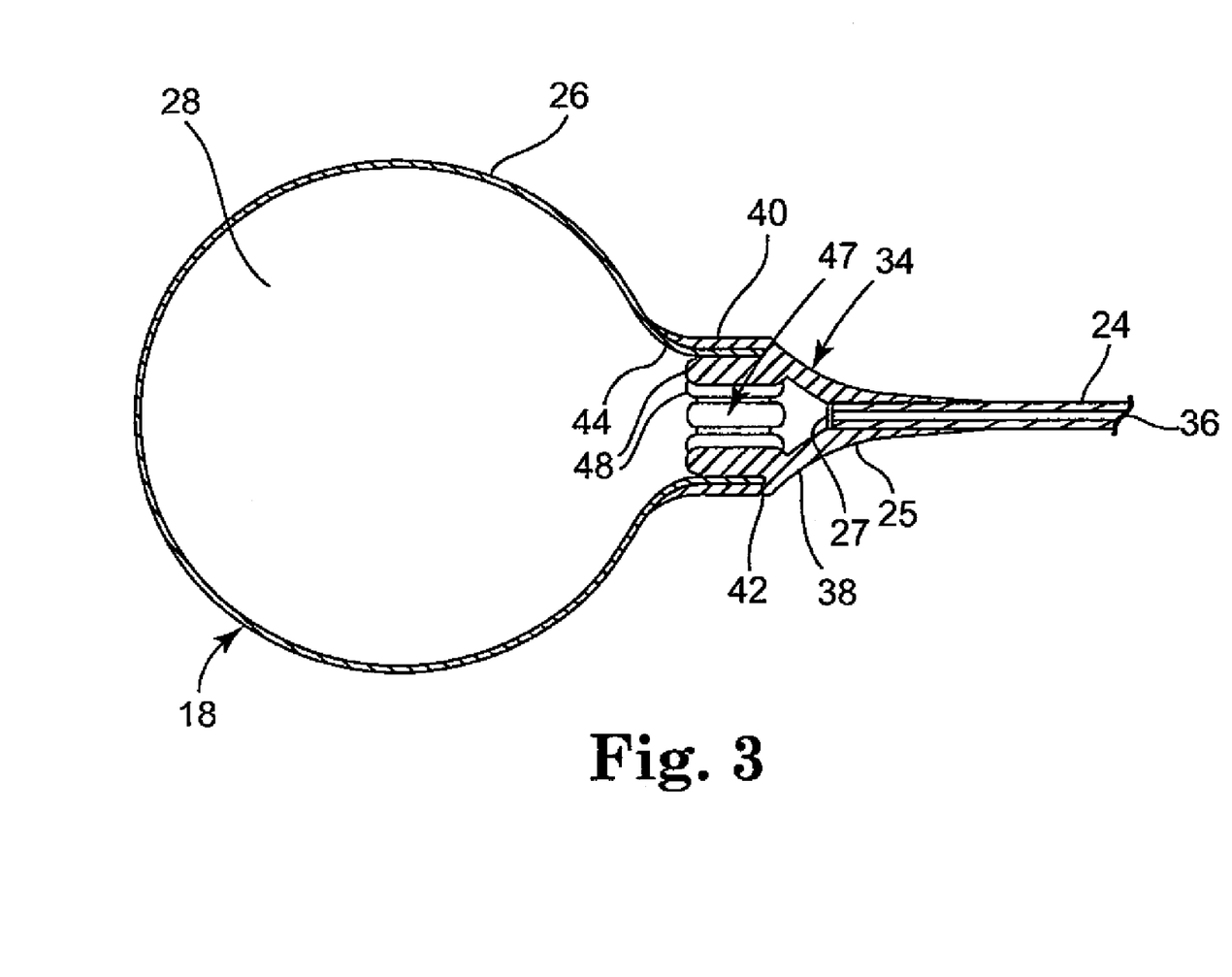
FIG. 3 is a cross-sectional side view of the reservoir of FIG. 2, showing a shell attached to a support structure or device of an adapter, and a tube attached to the adapter at a sleeve.

FIGS. 2 and 3 show one embodiment of the reservoir 18 of the present invention, which generally includes a shell 26 having an interior space 28 and an adapter 34 extending from the shell 26. Tube 24 is shown as extending from the adapter 34, although the tube 24 is not the only type of device that can extend from the reservoir 18 for fluid communication between the reservoir 18 and other adjacent devices or components. For example, additional or different adapters or devices may be connected directly to one end of the adapter 34, in which case any tubing used may optionally be attached to the configuration at some other point distal from the shell 26 and adapter 34. In cases where such a tube 24 is used, however, the tube 24 preferably includes an inner fluid passage 36 extending along its length through which fluid can move to and from the shell 26. Preferably, the tube 24 is a separate component that is sealed to the adapter 34 during a molding process as described below. However, the tube 24 may be molded as part of the adapter 34 or otherwise fused or bonded to the sleeve 25 of the adapter 34 with an appropriate technique.

Further, the adapter 34 may include an annular flange 40 adjacent the shell 26, and a sleeve 25 spaced from the shell 26, where the tube 24 may be attached to the adapter 34 at sleeve 25. The adapter 34 preferably includes an opening 27 adjacent to the fluid passage 36 that is configured to provide fluid communication between the tube 24 and the inner area of the annular flange 40. Thus, the opening 27 is preferably the same shape and size as the fluid passage 36 to allow fluid to move to and from the interior space 28 of shell 26 without fluid leakage between the components and to further allow fluid to move from the interior space 28 of the shell 26, through fluid passage 36, and to other components to which the tube 24 is attached. For example, referring to the exemplary device 10 of FIG. 1, the reservoir 18 can provide fluid to the pump 16 via tubing 24, and the pump can subsequently transfer fluid to and from the penile cylinders 12 and 14.

Figure 4:
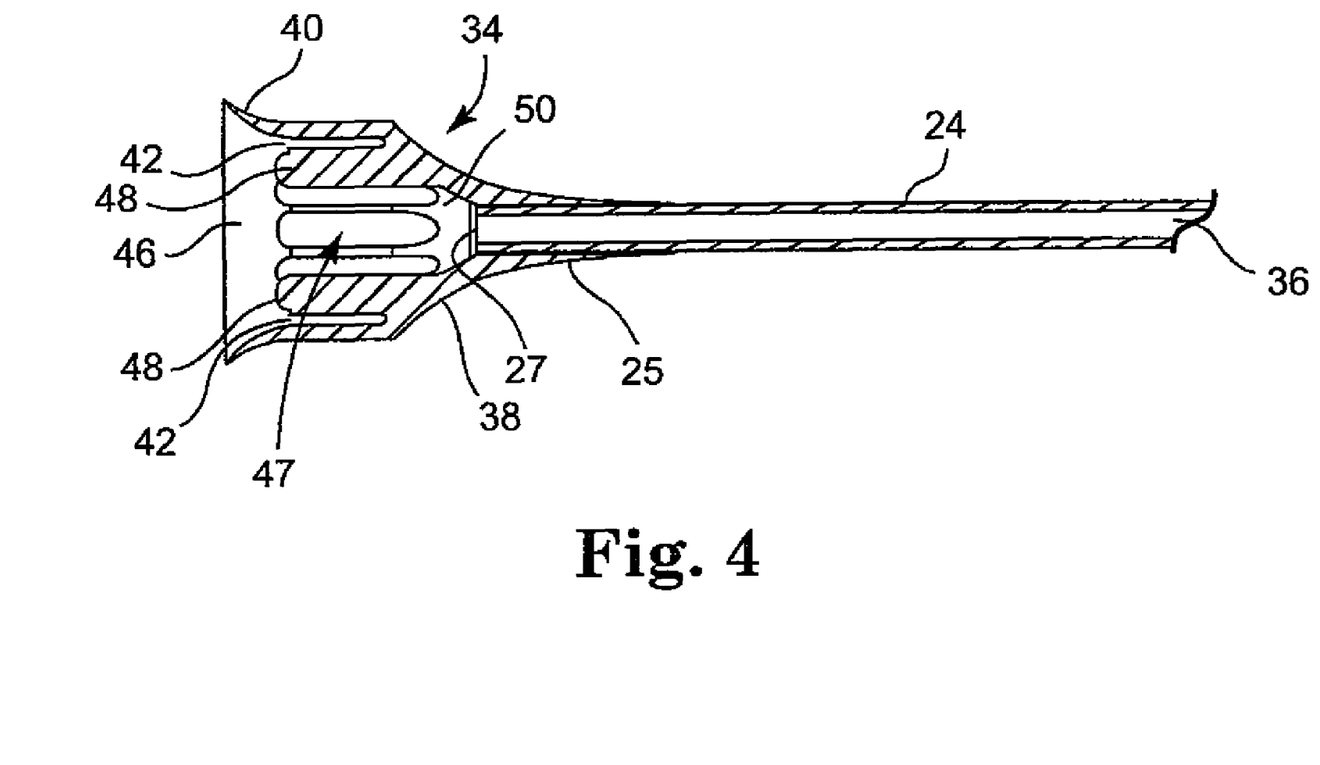
FIG. 4 is a cross-sectional side view of the adapter portion of FIG. 3, also including an extending tube.
Figure 5:
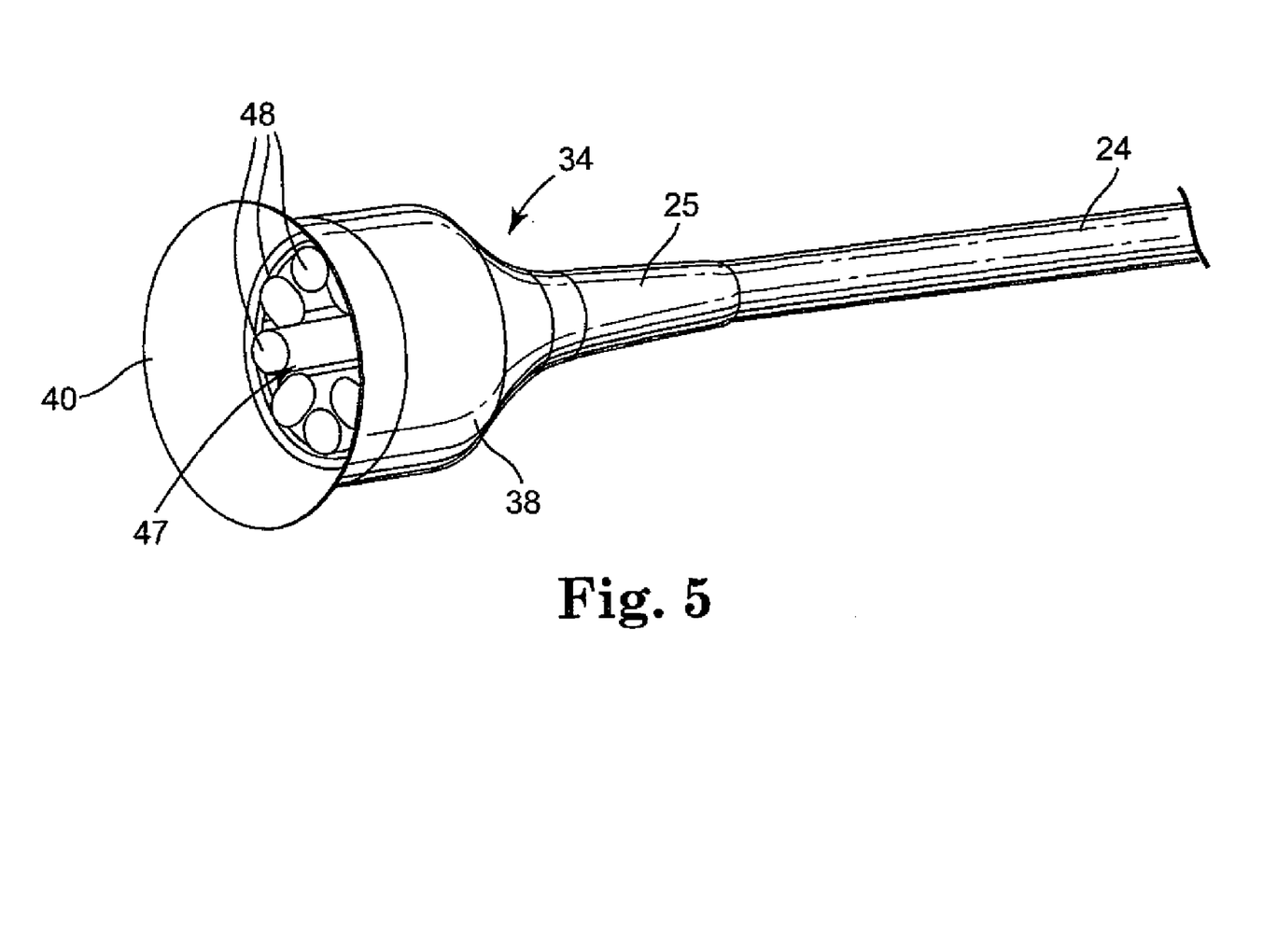
FIG. 5 is a perspective view of an adapter of the type shown in FIGS. 3 and 4.

Additionally referring to FIGS. 4 and 5, the adapter 34 is shown without an attached shell 26 to better illustrate the features of the adapter. As shown, the adapter 34 includes a body portion 38 and an annular flange 40. Preferably, the annular flange 40 increases in diameter from the area of the opening 27 in the adapter 34 toward the end of the flange 40. The body portion 38 also includes an annular groove 42 that is at least partially defined by the flange 40 and body portion 38, as illustrated. That is, the body portion 38 generally provides an interior surface of the groove 42 and an interior surface 46 of the flange 40 provides an exterior surface of the groove 42, where the exterior surface of the groove is spaced from the body portion 38 by a distance that corresponds with the desired width of the annular groove 42. The width of the groove 42 is preferably designed to accept the free edge of a shell of a reservoir assembly. Referring again to FIG. 3, the shell 26 preferably includes an annular neck portion 44 that fits into the annular groove 42. When the shell 26 is positioned so that its neck portion 44 is positioned within the groove 42, the interior surface 46 of the flange 40 will preferably be in contact with the outer surface of the shell 26. Thus, the flange 40 is preferably flexible enough that it can conform generally to the outside shape of the shell 26 in both its expanded and collapsed conditions. Further, when the neck portion 44 is positioned within the groove 42, the inside surface 46 of the flange 40 may be adhered or otherwise bonded to the outside surface of the shell 26 at the neck portion 44. In addition or alternatively, an outside surface of the body portion 38 may be bonded to an inside surface of the annular neck portion 44 in order to secure the shell 26 to the adapter 34. In addition, the inside surface 46 of the flange 40 may also be adhered to the portion of the shell 26 beyond the neck portion 44, such as where the diameter of the shell 26 increases and beyond the area where the neck portion 44 is positioned within the annular flange 40. It is contemplated that the thickness of the neck portion may vary and/or that the width of the annular gap may change along its length. For any portions of the reservoir components that are bonded to each other, any medical grade adhesive or the like may be used.

Referring again to FIGS. 3 and 4, the flange 40 is tapered in thickness as the flange 40 extends outwardly away from the body portion 38 so that the flange 40 is thickest in the area closest to the body portion 38, then tapers down to a smaller thickness when moving away from body portion 38. Preferably, the flange 40 tapers down to a point or small radius at its furthest position from the body portion 38 (i.e., the end of the flange 40). By using such a tapered flange 40, as shown, a smooth transition can be provided at the transition of the body portion 38 of the adapter 34 to the shell 26. Alternatively, the annular flange 40 may flare or splay further outward than is shown in FIG. 3. In this case, the neck of the shell should preferably be designed accordingly to mate with the annular flange and annular gap of the adapter without placing added stresses on the material of the flange and/or reservoir shell.

When a penile prosthesis device utilizing a reservoir 18 of the invention is implanted in a user, the shell 26 may be repeatedly deflated and inflated. During deflation, the shell 26 collapses inwardly on itself and flexes at the neck portion 44 (as well as at other parts of the shell 26). Such repeated flexing can cause fatigue at the neck portion 44, which could cause a gradual thinning of the wall and eventual failure (e.g., leakage) between the shell 26 and flange 40. Thus, the flange 40 is desirably configured to provide additional support at the neck portion 44 while also providing a smooth transition from the body portion 38 of the adapter 34 to the shell 26 and minimizing areas of stress concentration. In other words, at a point near the body portion 38 of the adapter 34, the neck portion 44 is preferably sealed or attached to the flange 40. The total wall thickness in this region near the body portion 38 thus includes the thickness of the flange 40 plus the thickness of the wall of the neck portion 44. However, the combined thickness of the flange 40 and the wall of the neck portion 44 will decrease at points that are spaced further from the body portion 38 due to the decrease in the flange thickness. Thus, as the flange 40 tapers down to its end or edge, the combined thickness gradually reduces or transitions to the thickness of the wall of the shell 26. This reduces compliance mismatch between the adapter 34 and the shell 26 and can provide improved reliability of the reservoir 18. Generally, compliance mismatch refers to a change in flexibility or compliance at a transition such as an abrupt transition from a thick section to a thin section. At such an abrupt transition, regions of concentrated stress may occur which could lead to premature fatigue and perhaps failure. The present invention thus provides a smooth and gradual transition between a portion of an adapter or base portion to a thinner portion of a shell or a reservoir.

Again referring to FIGS. 4 and 5, the adapter 34 preferably includes a support structure 47 that comprises a plurality of elements 48. The elements 48 are positioned within an interior space 50 of the body portion 38. In one preferred embodiment, the elements 48 are arranged circumferentially around the opening 27 to the fluid passage 36. The elements 48 preferably have a generally cylindrical shape as they extend away from the opening 27; however, the elements 48 may be any of a wide number of regular or irregular shaped structures. Each of the plurality of elements 48 within a particular adapter 34 may be shaped and sized to be identical to one another, or may instead have a different size, shape, and/or height from other adjacent elements 48.

The shells of the reservoirs of the present invention are generally shown as having a spherical, oval, or elliptical shape. However, the shell may instead have a more irregular or asymmetrical shape, or may include a shell that has another configuration, such as a shell that is more cylindrical in shape, kidney-shaped, disk-shaped, or shaped in some other way (with an appropriate size and material) so that the shell can expand or "inflate" to receive a desired amount of fluid. The shell shape should also contract or "deflate" with the removal of fluid from the reservoir. With any of the shapes chosen for the shell, an associated adapter should be designed to accommodate attachment of a portion of the shell to the adapter or molding of the shell adapter into one integral structure. For example, the flange portion may need to be more or less tapered to provide a smooth transition between the shell and adapter. The adapter may or may not include an annular gap in which a portion of the shell is positioned and attached, and other features of the shell and adapter may be designed to provide a shell and adapter that can expand and collapse in accordance with the present invention.

Because the devices in which reservoirs of the present invention are used will preferably be closed fluid systems, as fluid is transferred from a reservoir, the shell will collapse on itself as the penile cylinders inflate. The manner in which a shell, such as the shell 26, collapses or folds is generally unpredictable, so any part of the shell 26 could collapse toward the opening or orifice 27 and thereby restrict or block fluid flow through the passage 36 without the use of another configuration or structure. In use, the elements 48 can thus function to prevent the opening 27 from being blocked by some part of the shell 26 when it collapses due to fluid being moved from the reservoir 18 toward penile cylinders by a pump, for example. The elements 48 can prevent such flow problems and blockage because as the shell 26 collapses, one or more of the elements 48 will keep the shell 26 spaced from the opening 27, thereby preventing fluid flow blockages. Thus, it is preferable that the elements 48 are provided with at least a small space between them to allow sufficient fluid flow.

As such, fluid can flow between the spaced apart elements 48, even if a portion of the shell is resting on the elements 48. Further, the elements may be completely discrete components that individually extend from a base area, or may instead be molded or formed with at least some attachment between adjacent elements along the height of the elements. Variations of a flow control device or support device or structure other than that specifically shown in the figures of the present application may be used.

Figure 5A:
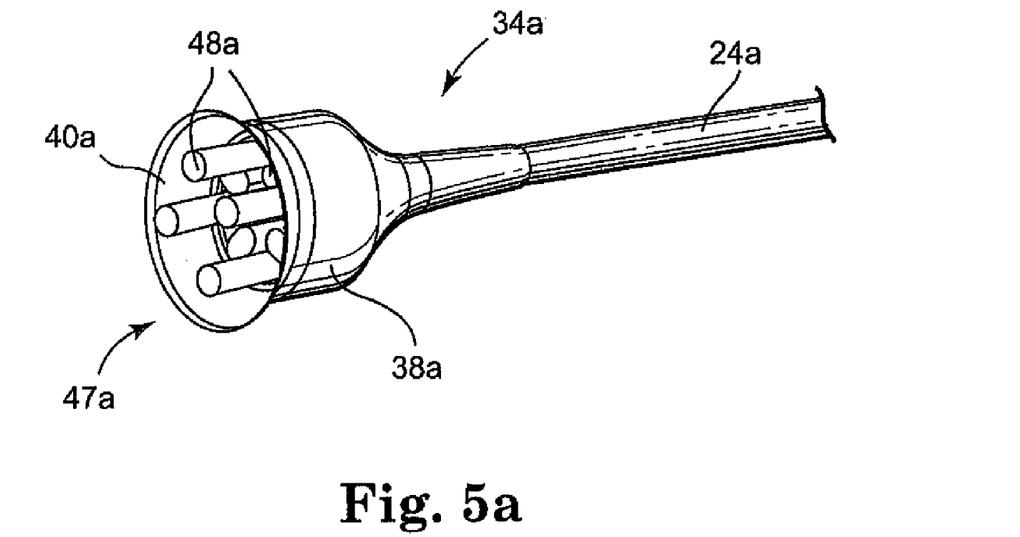
FIG. 5a is a perspective view of another embodiment of an adapter of the present invention, including a support structure having elongated elements alternating with shorter elements.

FIG. 5a illustrates another embodiment of an adapter 34a for use with a shell that can be attached thereto to make a reservoir assembly, where the adapter 34a includes a body portion 38a, an annular flange 40a, and a support structure 47a extending generally from the body portion 38a. The support structure 47a includes a plurality of elements 48a positioned within an interior space of the body portion 38a. In one preferred embodiment, the elements 48a are arranged circumferentially around the opening to a tube 24a that extends from the body portion 38a. As shown, this embodiment includes eight total elements 48a, with four of the elements 48a having the same height as each other, which is a greater height than that of the other four elements 48a, which also have the same height as each other. In this embodiment, the four elements 48a having the greater height actually extend beyond the end of the annular flange 40a, while the other four elements 48a do not extend beyond the end of the flange 40a. As shown, the elements 48a having the greater height are a different shape than those having the lesser height; however, any number of combinations of shapes and heights are considered to be within the scope of the present invention. For example, in the embodiment of FIG. 5a, all of the elements 48a may have identical cross-sections, or each of the elements 48a may have a different cross-section than each of the other elements 48a. Also, a given adapter may have elements with more than two heights, if desired. Additionally, as described herein relative to other embodiments of the invention, the selection of the number, configuration, height, and other features of the adapter elements is preferably selected to prevent or minimize blocking of fluid flow to and from an attached shell, and particularly to keep an attached shell from collapsing and blocking the fluid opening.

Figure 5B:
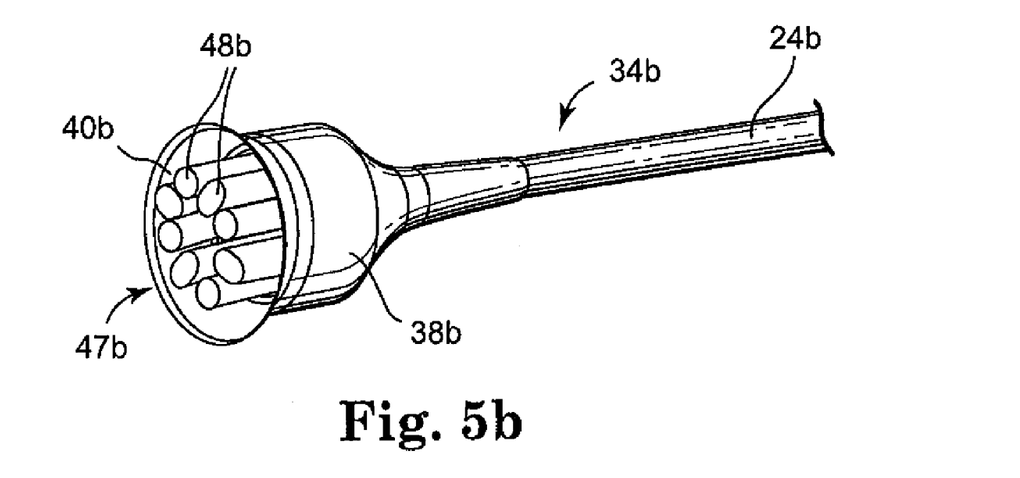
FIG. 5b is a perspective view of another embodiment of an adapter of the present invention, including a support structure having multiple elongated elements.

FIG. 5b illustrates another embodiment of an adapter 34b of the present invention. The adapter 34b again includes multiple elements 48b extending from a body portion 38b, where all of the elements 48b extend beyond the end of a flange 40b. In this case, alternating elements 48b have different cross-sections around the circumference of the body portion 38b such that half of the elements 48b have a circular cross-section and the other half of the elements 48b have an oval or elliptical cross-section. However, it is possible that all of the elements 48b have the same cross-sectional shape or that the group of elements 48b includes more than two different element shapes.

Figure 6:
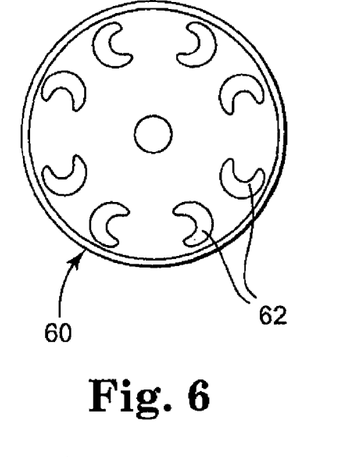
FIG. 6 is a schematic top view of another embodiment of an adapter having one arrangement of c-shaped elements in accordance with the present invention.
Figure 7:
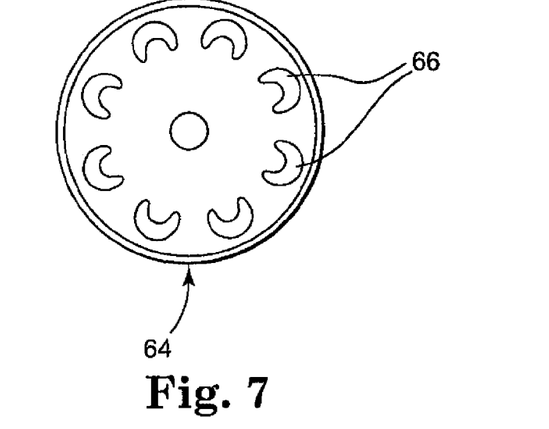
FIG. 7 is a schematic top view of another embodiment of an adapter having another arrangement of c-shaped elements in accordance with the present invention.

In FIG. 6, a schematic top view of another embodiment of an adapter 60 of the present invention is shown. The adapter 60 includes a plurality of c-shaped elements 62 that can be used as an alternative to the elements 48 shown in FIGS. 4 and 5. Elements 62 are arranged with the open portion of each c-shape facing another adjacent element 62 to advantageously provide channels for fluid to flow both between the elements and also within the c-shaped portion of the elements themselves. In FIG. 7, another embodiment of an adapter 64 is shown. The adapter 64 includes a plurality of c-shaped elements 66 that are arranged so that the c-shapes all face the center of the adapter 64. Again, these elements 66 are preferably arranged to provide channels for fluid flow between and within the individual elements 66.

Figure 8:
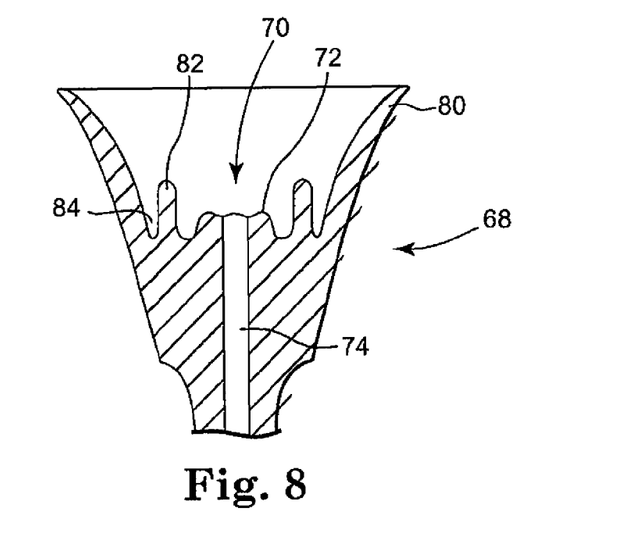
FIG. 8 is a schematic cross-sectional front view of another embodiment of a portion of an adapter of the present invention, showing a contoured support structure.

Also, in FIG. 8, a schematic cross-sectional view of another embodiment of an adapter 68 of the present invention is shown. The adapter 68 includes a support structure 70 having a textured or contoured surface 72 surrounding a fluid passage 74. The surface 72 may simply include such a contoured surface as shown, or alternatively may include some other type of contours or structures such as scallops, ridges, buttons, protrusions, bumps, channels, and/or other support structures that have the capability to hold or support at least a portion of a wall of a shell away from an opening to the fluid passage 74. In this way, the surface 72 allows fluid to flow through the passage 74 even if a portion of the shell collapses near the orifice of the fluid passage 74 inside an attached reservoir.

The adapter 68 further includes an annular flange 80 and an annular ridge portion 82, both of which are spaced from and circumferentially surround the fluid passage 74. Specifically, the ridge portion 82 is spaced from both the fluid passage 74 and the contoured surface 72 and preferably extends at least slightly beyond the surface 72 to further prevent an attached reservoir shell from collapsing onto and blocking the fluid passage 74 when the shell is at least partially deflated. The ridge portion 82 is also preferably spaced from the annular flange 80 to provide an annular groove 84 in which a portion of a shell may be received, such as described above relative to FIGS. 3 through 5. Such a shell position may also involve bonding or other types of attachments to secure a shell to the adapter 68.

Figure 15:
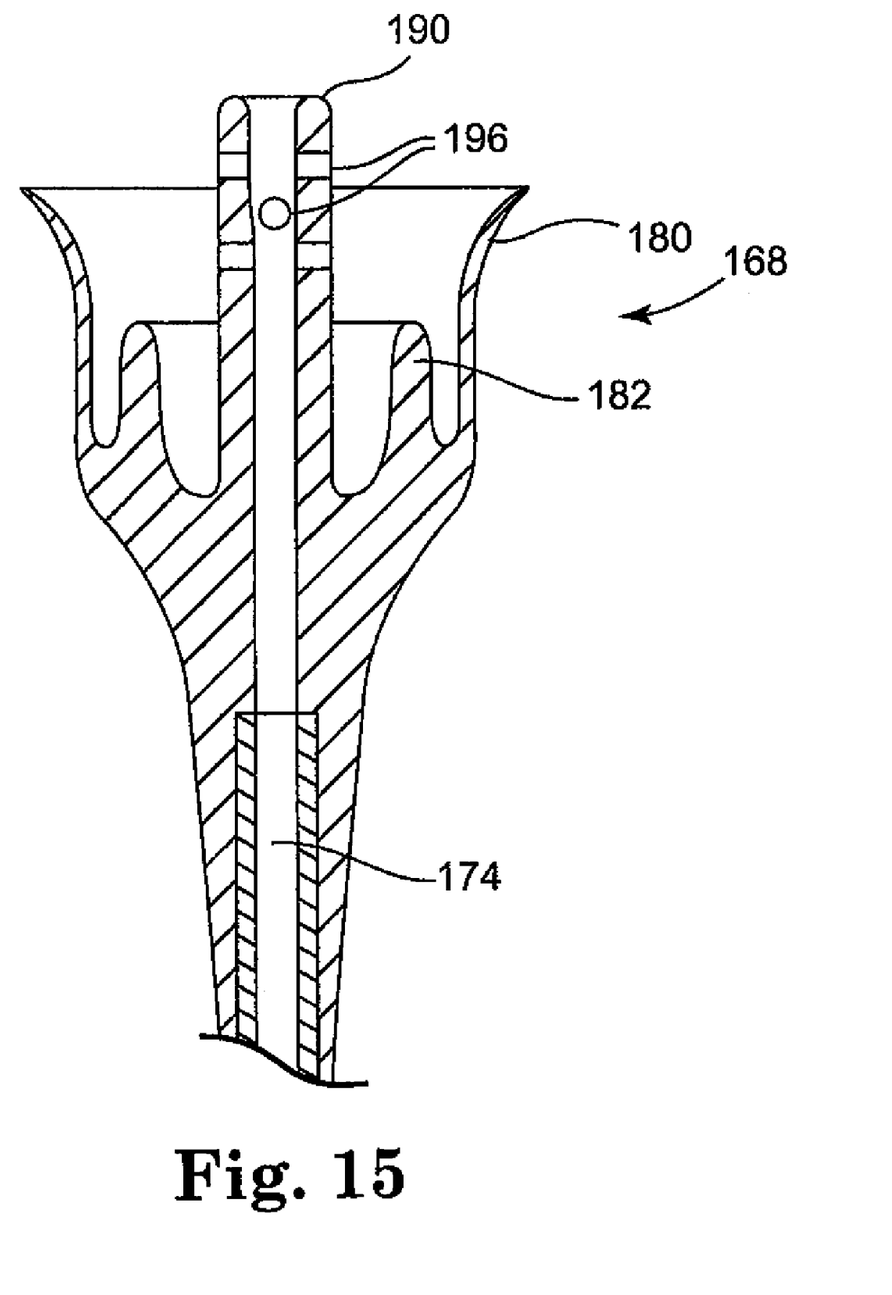
FIG. 15 is a partial cross-sectional front view of another embodiment of a portion of an adapter of the present invention having an elongated inner tubular structure.

Another embodiment of an adapter 168 is illustrated in FIG. 15 and includes a primary fluid passage 174 that extends generally through the center of the adapter 168. The adapter 168 further includes an annular flange 180 that is spaced from and circumferentially surrounds that passage 174, and an annular tube extension 190 that closely surrounds the passage 174. An additional annular ridge portion 182 may also optionally be included in the structure and positioned between the tube extension 190 and the flange 180. The tube extension 190 is preferably high enough to extend past the end of the annular flange 180, as shown, so that if an attached shell collapses, it will contact the tube extension 190. To promote fluid flow, the tube extension 190 also preferably includes a series of perforations or openings 196 through which fluid can flow for fluid movement between the fluid passage 174 and an attached shell. The perforations or openings 196 are preferably in direct fluid communication with the primary fluid passage 174 and the area immediately surrounding the extension 190, as shown. The perforations 196 may be sized and spaced around the circumference of tube extension 190 in any desired configuration that provides the desired fluid flow without compromising the strength of the tube extension (i.e., the extension 190 should not collapse or otherwise deform significantly).

The tube extension 190 may have either an open end that allows fluid to flow directly to and from the fluid passage 174 when a collapsed shell is not resting on the end of extension 190, or the tube extension 190 may instead have a closed end so that the only fluid communication with the fluid passage 174 is via the perforations 196. Further, when perforations or openings are used along the length of the extension 190, the perforations may have any of a wide variety of shapes and sizes, such as the circular shaped perforations 196 of FIG. 15. The number of perforations for a particular tube extension 190 may also vary, and the shape, locations, and spacing of the perforations may be different, depending on the configuration of the adapter. The tube extension 190 may optionally include a shaped feature at its end (e.g., a sphere, an ellipse, or the like) that will extend into the inner area of an attached reservoir shell. The shaped feature can help to maintain patency and minimize wear or damage to a collapsed shell that is supported on its surface. Whether or not such a feature is used, it is preferable that the surfaces of the tube extension 190 are relatively smooth and free from sharp edges that might damage a shell surface.

The tube extensions of the invention can be manufactured and assembled using a wide variety of methods. One example is to mold the tube extension as part of its associated adapter, so that the tube extension and adapter comprise one molded component. The tube extension may also be molded or extruded as a separate component that is bonded in some way to the adapter. The tube extension could also be over-molded onto the attached tubing, such that this dual-tube component could be bonded or attached to the adapter using any appropriate attachment or bonding method. When perforations are included in the tube extension, they can be made during the molding process or in a secondary operation after the tubing is manufactured.

While the embodiment of FIG. 15 particularly describes the use of perforations with a tube extension of an adapter, other embodiments of the present invention can likewise utilize perforations to provide additional fluid flow between the shell and a fluid passageway. For example, the elements 48 of FIG. 5 may include at least one perforation or opening and an associated fluid passageway that is in fluid communication with the fluid passageway 36 to provide an additional path for the fluid to move between the shell and fluid passageway.

Figure 9:
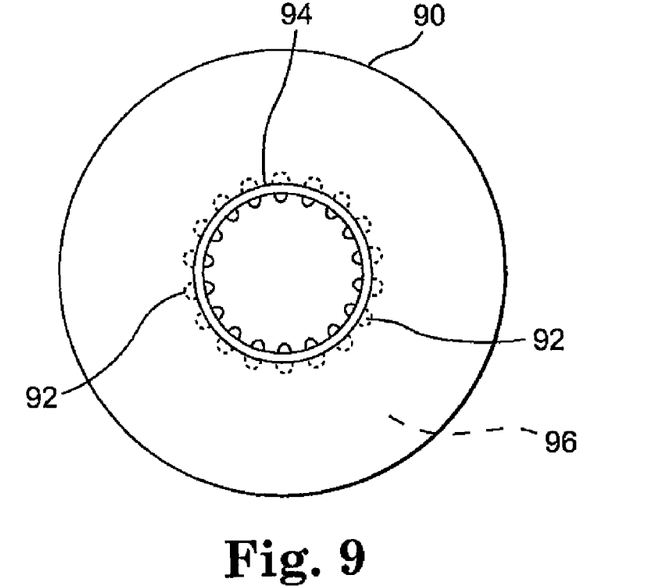
FIG. 9 is a bottom view of one embodiment of a portion of a reservoir shell, showing a neck portion having a plurality of circumferentially spaced elements.

In another aspect of the present invention, which is illustrated in FIG. 9, a shell 90 of a reservoir may include multiple structures or elements 92, such as ribs or protrusions, for controlling compliance mismatch between an adapter and the shell 90 for a multi-component reservoir. Such structures or elements 92 may also be used to control compliance mismatch for a reservoir where the adapter and shell are molded or formed as a single piece. Preferably, a plurality of elements 92 are spaced from each other around the circumference of the shell 90 in the area generally adjacent the neck portion 94 of the shell 90. However, the elements 92 may instead be positioned at the opening of the neck portion 94 (i.e., the edge or end of the shell 90) or further into the interior surface of the shell 90 such that they would not be visible when viewing the shell 90 from the edge of the neck. Such elements 92 can provide a smooth transition from an adapter or the like to the shell. That is, a gradually tapered wall thickness from an adapter or the like to a shell can be provided.

The elements 92 preferably protrude from the inner wall of the shell 90 toward an interior space 96 of the shell 90 and have at least a small space between adjacent elements to promote fluid flow, even when the shell is collapsed. The elements 92 may have any of a wide variety of configurations that provide the desired control of compliance mismatch between the shell and an adapter, such as cylinders or ribs that have the same or different dimensions along their lengths. In other words, the elements 92 may also have a tapered width or thickness along their lengths. The elements 92 may be any structure or surface that helps to transition at least a portion of an adapter or the like to a shell 90 by providing a smooth transition between the two, and preferably are shaped to provide a gradual transition from an adapter or the like. For example, the elements 92 may be formed as bumps or ridges or other outwardly extending features or the like. Preferably, the elements 92 are formed as spherical or elliptical or generally smooth curving structures in order to allow free flow of fluid while minimizing frictional resistance.

When a plurality of elements 92 are spaced circumferentially from each other, as described above, the elements 92 may be spaced apart at any desired distance, which will often be designed along with the number of elements used to achieve particular flow characteristics. For example, in one preferred arrangement, the spacing of the elements may be equal to or less than a width of each element. Additionally, the elements 92 preferably extend lengthwise along the neck portion 94 of a shell 90 and may extend beyond the neck portion 92 into a body portion of a shell 90.

Figure 10:
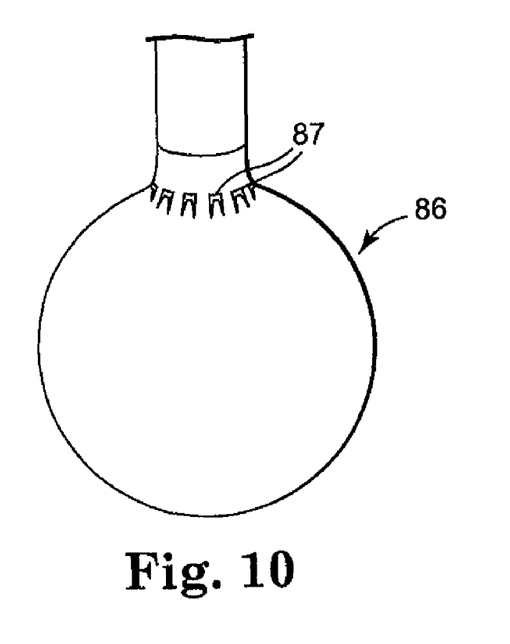
FIG. 10 is a perspective view of a portion of an embodiment of a reservoir of the present invention, including a plurality of indented regions circumferentially positioned around the neck region of the reservoir.

FIG. 10 illustrates another embodiment of a reservoir that includes features that can help to control (such as by reducing) compliance mismatch. The reservoir 86 of this figure includes multiple indented regions 87 spaced from one another that may form protrusions on an inside surface of the neck portion of the reservoir. The indented regions 87 are positioned near a transition between the neck and the body of the shell. As shown in FIG. 10, the indented regions 87 have a generally square shape; however, the regions 87 may instead have a wide variety of shapes and dimensions, such as a generally rectangular shape, a curved shape, or any other shape that provides the desired control of compliance mismatch between materials and/or material thicknesses that yield differently under applied loads. These features are preferably selected to promote patency through the fluid flow passage. The indented regions 87 may also be longer than shown so that they extend further onto the shell and/or neck regions of the reservoir, or may be shorter so that they do not extend as far onto the shell and/or neck regions of the reservoir. The indented regions 87 may be more or less recessed into the neck portion of the reservoir, depending on the desired properties of this region. Further, the use of these indented regions may be used alone or in combination with any of the other design features of the present invention described herein.

In another aspect of the invention, a lubricity enhancing coating such as a parylene coating or the like may be applied to at least a portion of an inside surface of a reservoir, such as is described relative to penile prosthesis components, for example, in U.S. Pat. No. 6,558,315 (Kuyava) and U.S. Patent Application Publication No. 2003/0220540 (Kuyava), both of which are commonly owned by the assignee of the present invention. Another example of the use of parylene coatings for artificial sphincters is further described, for example, in U.S. Patent Application Publication No. 2003/0028076 (Kuyava et al.), which is also commonly owned by the assignee of the present invention. A parylene coating may be applied by using conventionally known techniques such as vapor deposition or the like, for example. Such a lubricity enhancing coating can improve the frictional characteristics of an inside surface of a reservoir and the durability of the reservoir. This can improve reliability of a reservoir by controlling frictional effects on an inside surface of a reservoir that can result during inflation and deflation of such reservoirs.

In another aspect of the invention, at least some of the components of the penile implant devices can be coated on their outer surfaces with an antimicrobial agent, including the cylinders, pump and/or reservoir. Examples of coating antimicrobial agents on implantable medical devices are described, for example, in U.S. Pat. No. 6,534,112 (Bouchier et al.) and U.S. Patent Application Publication No. 2004/0040500 (Bouchier et al.), both of which are commonly owned by the assignee of the present invention.

Figure 11:
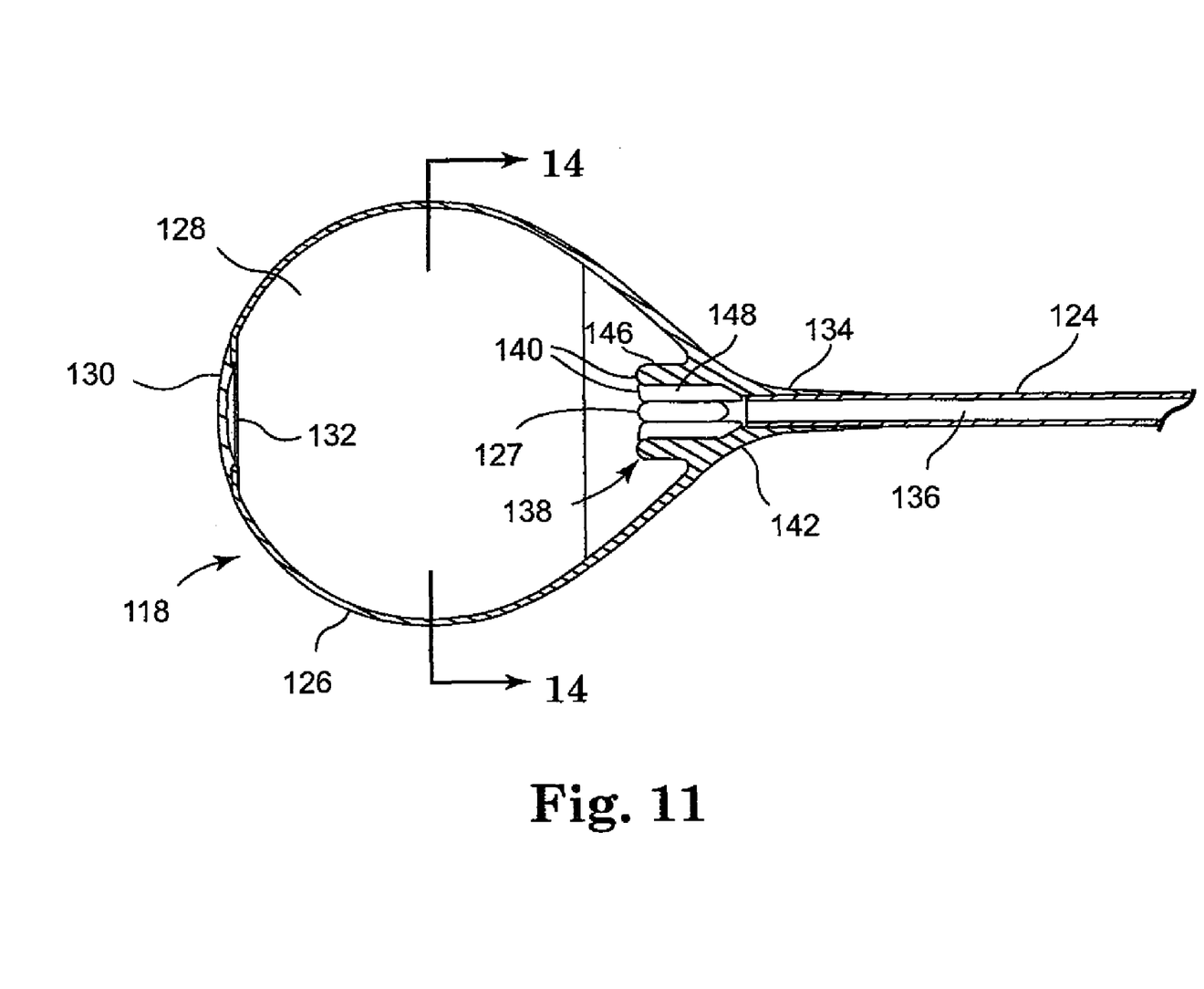
FIG. 11 is a cross-sectional view of another embodiment of a reservoir of the present invention, showing a body portion having a support device within an interior space of a shell, a cap closing an opening in the shell, and a tube attached to the shell at a sleeve.

FIG. 11 illustrates another embodiment of a reservoir 118 in accordance with the present invention, which can be used in the same types of implantable devices as described above, such as a three-piece penile prosthesis device of the type shown in FIG. 1, for example. As shown, the reservoir 118 includes a body portion or shell 126 having an interior space 128, an opening 132 at one end of the shell 126, and a cap 130 that is positioned to close or seal the opening 132 in the shell 126. The reservoir 118 further includes a sleeve portion or adapter 134 extending from the shell 126. Tube 124 extends from the sleeve portion 134 in this embodiment; however, it is possible that the sleeve portion 134 instead is fluidly connected to some other components or devices without the use of tubing, such as tube 124. In cases where such a tube 124 is used, the tube 124 preferably includes an inner fluid passage 136 extending along its length through which fluid can move to and from the interior space 128 of the shell 126. The reservoir 118 further includes a support structure 138 within the interior space 128 of the shell 126.

As shown in FIG. 11, the sleeve portion 134 is coupled with the tube 124 to define the fluid passage 136 for moving fluid to and from the interior space 128 of the body portion 126. Fluid can move from the interior space 128, through fluid passage 136, and to other components to which the tube 124 is attached. For example, referring to the exemplary device 10 of FIG. 1, the reservoir can supply fluid to the pump 16 via tubing 24, which can subsequently transfer fluid to and from the penile cylinders 12 and 14. Preferably, the tube 124 of FIG. 11 is a separate component that is sealed to the sleeve portion 134 during the molding process as described below. However, the tube 124 may be molded as part of the shell 126 or otherwise fused or bonded to the sleeve portion 134 with an appropriate technique.

Figure 12:
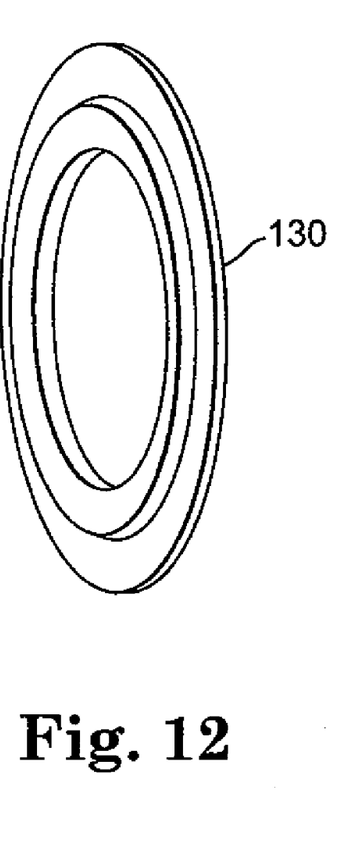
FIG. 12 is a perspective view of a cap of the type that can be used to close or seal the opening in the shell of the reservoir of FIG. 11.
Figure 13:
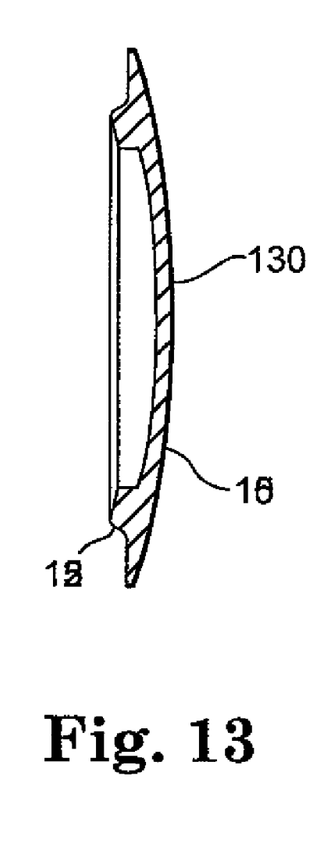
FIG. 13 is a cross-sectional view of the cap of FIG. 12.

A perspective view of one embodiment of the cap 130 is shown in FIG. 12 and a cross-sectional view of that cap 130 is shown in FIG. 13. As described below, the opening 132 of the shell 126 is created due to the processes used for molding the reservoir 118 of this embodiment, which includes using this opening 132 to remove a mold after the reservoir 118 is formed. In order to seal this opening 132 and make the shell 126 into a closed volume, the cap 130 can be used to completely cover the opening 132, such as with a suitable adhesive or the like, to provide a fluid-tight seal. For example, medical grade silicone adhesive or the like may be used. As shown, the cap 130 preferably includes a curved outer surface 150 that generally matches the curve of the shell 126 so that the surface 150 essentially makes the shell 126 into a continuous, smooth structure. In addition, the cap 130 also preferably has an insertable portion 152 that has a smaller diameter than that of the curved surface 150, where the diameter of the insertable portion 152 is generally the same as the diameter of the opening 132 in the shell 126.

In preferred embodiments of the invention, the reservoir 118 (and specifically the interior space 128 of the shell 126) includes a support structure positioned near an exit area or orifice 127 of the shell 126. In particular, the support structure 138 is preferably positioned to be generally opposite the opening 132 and cap 130 of the shell 126. During use, liquid inside the reservoir 118 can transfer fluid from its interior space 128 to fill the inflatable cylinders of the prosthesis. As fluid exits the shell 126, the reservoir 118 empties with an attendant collapse of the flexible walls of the shell around the volume of the displaced liquid. This collapse is due to the flexible material from which the shell 126 is preferably designed and the various pressures that are placed on the outside of the shell 126 from the user's bodily organs, fluids and the like, along with fluid pressures within the system that tend to create a negative pressure within the reservoir 118 as fluid is transferred from the interior space 128. It is preferred that when the shell 126 of the reservoir 118 collapses on itself, that the internal surface of the shell 126 does not partially or completely cover the exit orifice 127 and interfere with flow of the fluid through the exit orifice 127. A support structure according to the invention is thus used to prevent such blockage of the orifice 127 and is preferably a structure that, during use, prevents the internal surfaces of the shell 126 from covering the exit orifice 127. The particular form and shape of the support structure can include a wide variety of configurations, such as a number of elements or protrusions of the same or different shapes and sizes arranged around the exit orifice 137. The elements may be relatively round or oval or otherwise shaped in cross section, of the same or different sizes, or of irregular shapes.

Figure 14:
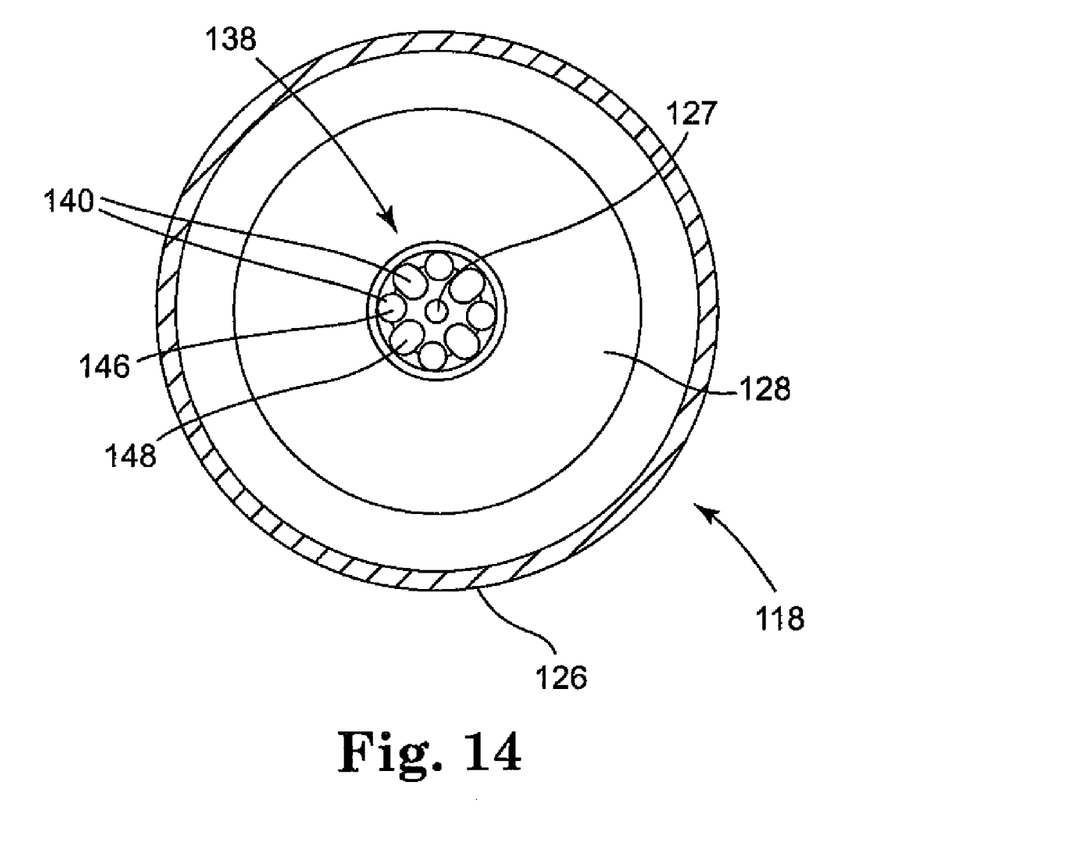
FIG. 14 is a cross-sectional view of the reservoir of FIG. 11 taken along the line 14-14.

Referring to FIGS. 11 and 14, one particular embodiment of the support structure 138 includes a plurality of elements 140 that extend from a base portion 142 of the shell 126 of the reservoir 118. The elements 140 are positioned within the interior space 128 of the shell 126. Referring to FIG. 14 in particular, multiple elements 140 are arranged circumferentially around orifice 127, preferably with at least a small space or gap between adjacent elements 140. In this embodiment, the support structure 138 specifically includes four cylindrically shaped protrusions 146 that have a generally circular cross-section as they extend away from the base portion 142. The support structure 138 of this embodiment also includes four elements 148 that have a cross-sectional shape different from that of elements 146. As shown, the elements 148 have a width similar to the diameter of elements 146 and a length that is greater than the radius of elements 146. Elements 146 and 148 are arranged to alternate with each other around orifice 127 such that there is a gap between each adjacent elements 146 and 148. The different cross-sectional shapes of the alternating adjacent elements are preferably selected and designed to prevent or minimize the elements 146 and 148 from themselves becoming squeezed together or otherwise collapsing into themselves and blocking or inhibiting flow of fluid through orifice 127.

In use, a support structure, such as the illustrated support structure 138, can function to prevent orifice 127 from becoming blocked or closed by some part of the shell 126 as fluid moves from reservoir 118 to penile prostheses and the shell 126 collapses on itself. Without a support structure of the type described herein, the manner in which a shell (such as shell 126) collapses or folds is generally unpredictable so any part of the shell 126 could collapse onto orifice 127 and thereby restrict or block fluid flow through the passage 136. A support structure according to the invention can prevent such flow problems because as the shell 126 collapses, the shell 126 can be supported or held at a distance away from the orifice 127 by the support structure (e.g., protrusions 146 and 148). Fluid can then flow through the orifice 137 between the elements 146 and 148.

As shown in the exemplary reservoir 118 of FIGS. 11 and 14, the shell 126, sleeve 134, and support structure 138 are preferably formed as an integral structure (i.e., a single piece construction); however, it is possible that the components are arranged as separate components that are connected or attached to each other. In any case, the tube 124 of this embodiment is preferably formed as a separate structure that is attached to sleeve 134 as described below. As described above, cap 130 is also formed as a separate structure that is attached to shell 126 when desired.

When the shell 126, sleeve 134, and support structure 138 are made of a single piece, the configuration may be formed by injection molding. Methods of injection molding may include the use of a flowable material (e.g., thermoplastic or thermosetting), such as a polymeric material, and a mold. The flowable material is placed at a desired temperature (e.g., by heating) and is injected into a cavity to produce a molded component (here, a fluid reservoir). The mold is then opened, optionally after cooling, and the molded component can be removed from the mold and optionally cured. In particularly preferred embodiments, a reservoir can be prepared by injection molding methods, wherein the reservoir includes a shell, a sleeve, and support structure. The reservoir may be molded to become attached to a tube at the exit orifice of the reservoir shell. That is, by preferred injection molding processes, an elongated tube, such as tube 124, can be attached to the reservoir during a process of injection molding the reservoir. To do this, the tube can be positioned onto a mandrel of a mold. A relatively spherical, solid mold core pin is also included, which is a form for the inside of the reservoir. Outer sections of the mold that define the outer surfaces of the reservoir are then placed around the core pin to thereby create a cavity that is the size and shape of the fluid reservoir (including the sleeve and support device). The entire mold is then brought to a processing temperature, then a predetermined amount of a desired material is injected into the mold over the tube and the spherical mold core pin to fill the cavity. After a predetermined time, the mold is opened and the reservoir with the attached tube is removed from the mold, with the sleeve thereby becoming molded around the outside diameter of the tube as the sleeve body portions of the reservoir are formed.

The reservoir, being of a flexible material, can be removed from around the core pin following cooling or curing of the flexible material as necessary. Removal of the reservoir from the core pin can be done by stretching the reservoir material around the core pin. Optionally, water, soap, air, or a combination of these, can be used to separate the inside surface of the reservoir from the core pin. One especially convenient and effective way to introduce any of water, soap, and air, to the space between the core pin and the inside of the reservoir, is to inject any one or more of these through the tube connected to the reservoir.

As one example, a reservoir may be made from liquid silicone rubber. A mold temperature in the range of 250° F. (121° C.) to 275° F. (135° C.) may be used. Also, a molding time of approximately 2.5 minutes may be used. Alternatively, the reservoir may be made from any other useful, flexible medical or industrial material that is biologically inert and non-reactive with the inflating fluid that will be contained by the reservoir. The material may be thermosetting or thermoplastic. Specific examples of useful materials can include thermosetting silicone rubber (e.g., polydimethyl siloxane), thermosetting or thermoplastic urethanes, C-flex, santoprene thermoplastics, and the like.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

We claim:

1. A method of making a fluid reservoir for use in a penile prosthesis device, the method comprising the steps of:
    providing a mold having a cavity, wherein the cavity defines the surfaces of:
        a reservoir shell having an inner fluid storage area;
        a sleeve extending from the shell; and
        a support structure extending from the sleeve at least partially into the inner fluid storage area;
    injecting flowable material into the cavity of the mold;
    curing the material in the cavity of the mold for a predetermined period of time; and
    removing the cured fluid reservoir from the mold.

2. The method of claim 1, further comprising the step of positioning an elongated tube within the mold cavity prior to injecting the flowable material into the cavity.

3. The method of claim 1, further comprising the step of positioning a mold core pin within the mold cavity prior to injecting the flowable material into the cavity to create a space between the mold core pin and the mold cavity that defines the surfaces of the fluid reservoir, wherein the step of injecting flowable material includes injecting the flowable material into the space between the mold core pin and the mold cavity.

4. The method of claim 3, further comprising the step of removing the molded fluid reservoir from the mold core pin by stretching the reservoir around the core pin.

5. The method of claim 4, wherein the step of removing the molded fluid reservoir from the mold core pin further includes the step of introducing a material into the space between the molded reservoir and the core pin to facilitate separation of the reservoir from the core pin.

6. The method of claim 5, wherein the material introduced to separate the reservoir from the core pin includes at least one of water, soap, and air.

* * * * *